(12) United States Patent
Jang et al.

(10) Patent No.: US 10,660,940 B2
(45) Date of Patent: May 26, 2020

(54) PREPARATION METHOD FOR HIGH-YIELD PRODUCTION OF PHYSIOLOGICALLY ACTIVE POLYPEPTIDE CONJUGATE

(71) Applicant: HANMI PHARM. CO., LTD., Hwaseong-si, Gyeonggi-do (KR)

(72) Inventors: Myung Hyun Jang, Seoul (KR); Min Young Kim, Suwon-si (KR); Dae Jin Kim, Hwaseong-si (KR); Sung Youb Jung, Yongin-si (KR); Se Chang Kwon, Seoul (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 209 days.

(21) Appl. No.: 14/772,493

(22) PCT Filed: Mar. 5, 2014

(86) PCT No.: PCT/KR2014/001818
§ 371 (c)(1),
(2) Date: Sep. 3, 2015

(87) PCT Pub. No.: WO2014/137161
PCT Pub. Date: Sep. 12, 2014

(65) Prior Publication Data
US 2016/0008484 A1    Jan. 14, 2016

(30) Foreign Application Priority Data
Mar. 5, 2013   (KR) .................. 10-2013-0023602

(51) Int. Cl.
*A61K 47/68* (2017.01)
*G01N 33/53* (2006.01)
*A61K 38/28* (2006.01)
*C07K 1/107* (2006.01)
*C07K 14/62* (2006.01)

(52) U.S. Cl.
CPC .............. *A61K 38/28* (2013.01); *A61K 47/68* (2017.08); *A61K 47/6811* (2017.08); *C07K 1/1077* (2013.01); *C07K 14/62* (2013.01); *C07K 2319/30* (2013.01)

(58) Field of Classification Search
CPC .......... A61K 47/6811; A61K 47/6813; A61K 47/6815; A61K 47/60; A61K 38/28; A61K 47/68; A61K 47/48215; C07K 14/62; C07K 1/1077; C07K 2319/30; G01N 33/5306; G01N 33/563
See application file for complete search history.

(56) References Cited

U.S. PATENT DOCUMENTS 6,384,195 B1    5/2002  Delgado et al.

FOREIGN PATENT DOCUMENTS

| CN | 1723219 A | 1/2006 |
|---|---|---|
| CN | 102112493 A | 6/2011 |
| EP | 1967212 A2 | 9/2008 |
| JP | 2006519238 A | 8/2006 |
| JP | 2007536211 A | 12/2007 |
| JP | 2011519361 A | 7/2011 |
| KR | 10-2005-0047032 A | 5/2005 |
| KR | 10-2011-0134210 A | 12/2011 |
| WO | 01/83525 A2 | 11/2001 |
| WO | 2005/047336 A1 | 5/2005 |
| WO | 2005047334 A1 | 5/2005 |
| WO | 2010011096 A2 | 1/2010 |
| WO | 2010/078376 A2 | 7/2010 |
| WO | 2011/122921 A2 | 10/2011 |

OTHER PUBLICATIONS

European Patent Office, Communication dated Sep. 22, 2016, issued in counterpart European Application No. 14760968.9.
Communication dated May 10, 2016 from the Intellectual Property Office of Singapore in counterpart Application No. 11201506937R.
Eizo Sada, et al., "Resistance to Proteolysis of Antibody Ligands Modified with Polyethylene Glycol", Journal of Fermentation and Bioengineering, 1991, pp. 137-139, vol. 71, No. 2.
International Searching Authority, International Search Report of PCT/KR2014/001818, dated Jun. 24, 2014. [PCT/ISA/210].
International Searching Authority, Written Opinion of PCT/KR2014/001818, dated Jun. 24, 2014. [PCT/ISA/237].
Intellectual Property Office of Singapore, Communication dated Dec. 12, 2016 in counterpart Application No. 11201506937R.
Japanese Patent Office; Communication dated Nov. 28, 2017 in counterpart application No. 2015-561270.
State Intellectual Property Office of People's Republic of China; Communication dated Mar. 13, 2018 in counterpart Chinese application No. 201480011914.6.
Intellectual Property Office of Taiwan; Communication dated Apr. 30, 2018 in counterpart Taiwanese application No. 103107577.

*Primary Examiner* — Phuong Huynh
(74) *Attorney, Agent, or Firm* — Sughrue Mion, PLLC

(57) ABSTRACT

A method for preparing a conjugate by linking a physiologically active polypeptide, a non-peptidyl polymer linker, and an immunoglobulin constant region via a covalent bond are disclosed. The method enables an efficient preparation of a physiologically active polypeptide conjugate, in which a salt is used in a coupling reaction to improve the problem of low production yield during preparation of the physiologically active polypeptide conjugate.

28 Claims, 1 Drawing Sheet
Specification includes a Sequence Listing.

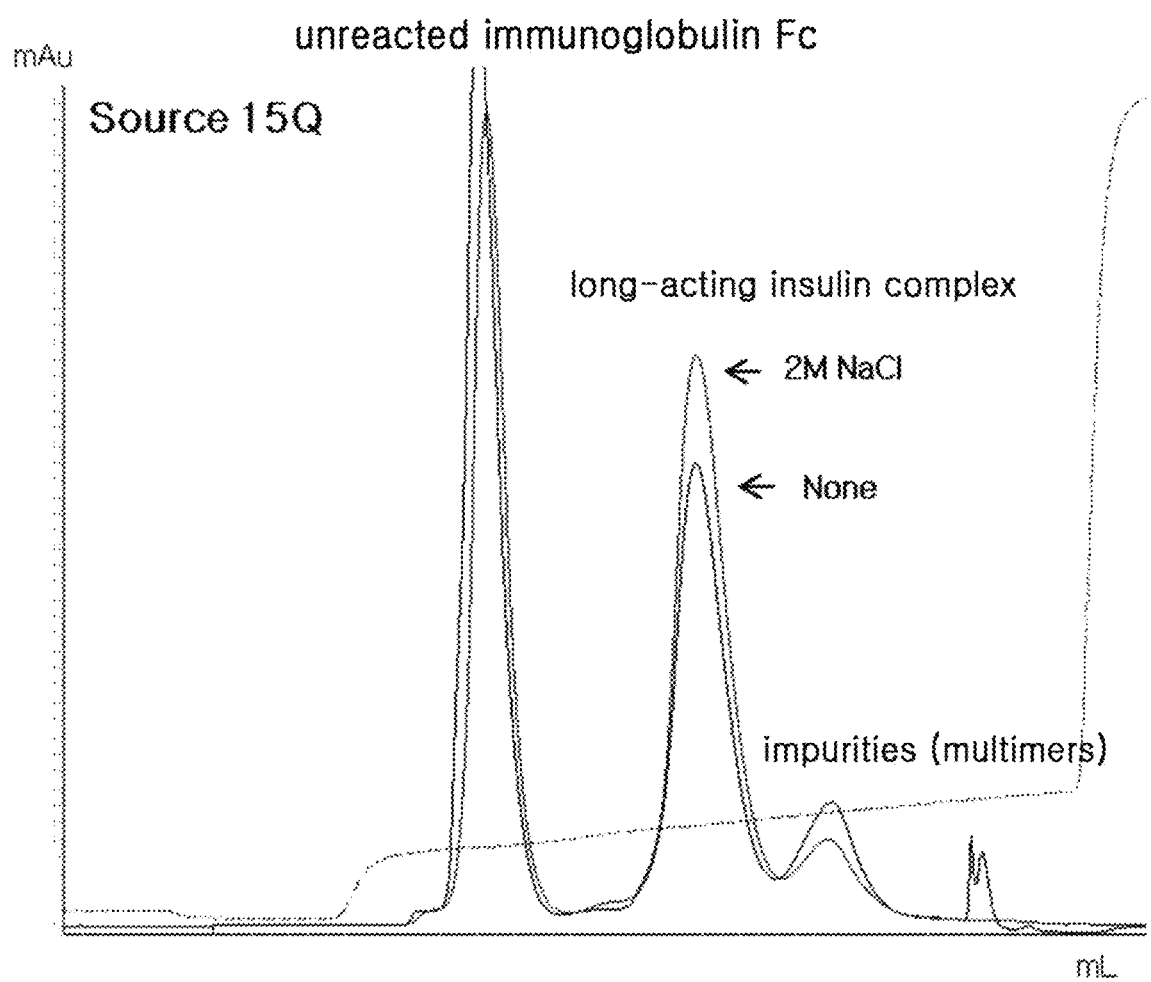

PREPARATION METHOD FOR HIGH-YIELD PRODUCTION OF PHYSIOLOGICALLY ACTIVE POLYPEPTIDE CONJUGATE

CROSS REFERENCE TO RELATED APPLICATIONS

This application is a National Stage of International Application No. PCT/KR2014/001818 filed Mar. 5, 2014, claiming priority based on Korean Patent Application No. 10-2013-0023602, filed Mar. 5, 2013, the contents of all of which are incorporated herein by reference in their entirety.

BACKGROUND OF THE INVENTION

1. Field of the Invention

The present invention relates to a method for preparing a conjugate by linking a physiologically active polypeptide, a non-peptidyl polymer linker, and an immunoglobulin constant region via a covalent bond. More particularly, the present invention relates to a method for efficiently preparing the physiologically active polypeptide conjugate, in which a salt is used in a coupling reaction to improve the problem of low production yield during preparation of the physiologically active polypeptide conjugate.

2. Description of the Related Art

In general, physiologically active polypeptides are easy to denature owing to their low stability and are decomposed by protein hydrolase in blood to be readily removed through the kidney or liver. Therefore, in order to maintain the blood concentration and potency of protein medicines including a physiologically active polypeptide as the pharmacological active ingredient, it is necessary to frequently administer the protein-based drug to patients. However, in the case of protein medicines administered to patients primarily in the form of an injectable formulation, frequent injections to maintain the blood concentration of physiologically active polypeptides may cause excessive suffering in patients and high treatment cost. To solve such problems, there has been constant effort to maximize pharmacological efficacy by increasing the blood stability of protein drugs and maintaining the blood drug concentration for a longer time. Such long-acting formulations of protein drugs are required to increase the stability of protein drugs and at the same time to maintain the potency of the drugs themselves at a sufficiently high level, as well as to cause no immune reaction in patients.

In the prior art, for stabilizing proteins and inhibiting contact with protein hydrolase and loss through the kidney, a method for chemically adding polymers having a high solubility such as polyethylene glycol (hereinafter, referred to as "PEG") to the surface of protein drugs has been used. It has been known that PEGs are effective in stabilizing proteins and preventing the hydrolysis of proteins by non-specifically binding PEG to a specific site or various sites of the target protein to increase the solubility of the protein, and do not cause any adverse side effects (Sada et al., J. Fermentation Bioengineering 71: 137-139, 1991).

However, in the method using PEG, despite its capability to enhance circulation time of peptide drugs by increasing the molecular weight of PEG, the potency of the peptide drug is significantly lowered and the reactivity of PEG with peptides is lowered concurrent with an increase in the molecular weight, thereby reducing the yield.

Further, a method for preparing a fusion protein of an immunoglobulin fragment and a physiologically active polypeptide can overcome the problems of low pegylation yield and non-specificity, but has problems that the increase of the blood half-life is not remarkably high, contrary to expectation, and in some cases, it possesses low titer. In order to maximize the effect of increasing the blood half-life, various kinds of peptide linkers can also be used, but may have a possibility of inducing an immunological reaction. In addition, there are problems in that, in cases where peptides having disulfide bonds, such as BNP, are used, application is difficult due to high misfolding probability, and in cases where non-native amino acid residues are present, production is impossible in the form of a genetic recombinant.

Insulin is a peptide secreted from the beta cells of human pancreas as a material which plays a very important role in controlling the blood glucose level in the body. In cases where insulin is not properly secreted or insulin as secreted does not properly act in the body, blood glucose in the body cannot be controlled and is increased, thereby inducing the state referred to as diabetes. The case as stated above is referred to as type 2 diabetes mellitus, and the case where insulin is not secreted from the pancreas to increase blood glucose is referred to as type 1 diabetes mellitus. Type 2 diabetes mellitus is treated with an oral hypoglycemic agent including a chemical material as the main component, and in certain patients, is also treated with insulin. On the other hand, treatment of type 1 diabetes mellitus necessarily requires the administration of insulin.

Insulin therapy as widely used at the present time is a method of administering insulin via injection before and after meals. However, such insulin therapy requires that insulin be constantly administered three times daily, and therefore causes much suffering and inconvenience to patients. In order to overcome such problems, various attempts have been made. One of them has been an attempt to deliver peptide drugs into the body by way of inhalation through oral or nasal cavities by increasing the biological membrane permeability of peptide drugs. However, such a method has a significantly lower delivery efficiency in the body as compared to injection, and therefore there are many difficulties as yet in maintaining the in vivo activity of peptide drugs in the required conditions.

Further, methods for delaying absorption after subcutaneous administration of excessive drugs has been attempted. According to this, methods for maintaining blood drug concentration through only a single administration daily has been reported. Some have been approved as a medicinal product (e.g. Lantus, Sanofi-aventis) and are administered to patients at the present time. The research has progressed to modify insulin with fatty acids to strengthen the binding of insulin polymer and to extend the duration through binding to albumin present at the site of administration and in blood, and drugs produced using such a method have been approved as medicinal products (Levemir, NovoNordisk). However, such methods have the side effect of causing a pain at the site of administration, and additionally, the administration interval of a single injection daily still lays a significant burden on patients.

In order to solve these problems, the present inventors prepared a conjugate comprising a physiologically active polypeptide and an immunoglobulin constant region using a non-peptidyl polymer as a linker, as a strategy to simultaneously maximize an increase of blood half-life and maintenance of in vivo activity of physiologically active polypeptides including insulin. However, a method of preparing the conjugate with high yield and purity is still required, because the raw materials constituting the conjugate are expensive. Under this background, the present inventors found that when a proper type and concentration of a salt is added to a reaction solution in a coupling reaction step during preparation of the conjugate, a conjugate of a physiologically active polypeptide can be prepared with high yield and purity and production costs can be reduced, thereby completing the present invention.

SUMMARY OF THE INVENTION

An object of the present invention is to provide an efficient method capable of improving low production yield during preparation of a conjugate by linking a physiologically active polypeptide, a non-peptidyl polymer linker, and an immunoglobulin constant region via a covalent bond.

In one aspect to achieve the above object, the present invention provides a method for preparing a conjugate of physiologically active polypeptide-non-peptidyl polymer-immunoglobulin constant region, comprising the steps of: (1) reacting a non-peptidyl polymer with one of a physiologically active polypeptide or an immunoglobulin constant region; and (2) reacting the reaction mixture of step (1) with the other of the physiologically active polypeptide or the immunoglobulin constant region in the presence of a salt.

Preferably, the non-peptidyl polymer may have each independently a functional group selected from the group consisting of an aldehyde derivative, a maleimide derivative and a succinimide derivative at both ends thereof.

More preferably, the non-peptidyl polymer may be linked to the physiologically active polypeptide and the immunoglobulin constant region via the functional groups at both ends thereof to form a covalent bond.

Preferably, the method may further comprise the step of separating a complex of physiologically active polypeptide-non-peptidyl polymer or a complex of immunoglobulin constant region-non-peptidyl polymer from the reaction mixture after step (1).

Preferably, the salt may be selected from the group consisting of sodium chloride, sodium acetate, sodium sulfate, sodium phosphate, sodium carbonate, sodium cyanide, sodium citrate, sodium nitrate, potassium chloride, potassium acetate, potassium sulfate, potassium phosphate, potassium carbonate, potassium cyanide, potassium citrate, potassium nitrate, magnesium chloride, magnesium acetate, magnesium sulfate, magnesium phosphate, magnesium carbonate, magnesium cyanide, magnesium citrate, magnesium nitrate, ammonium phosphate, ammonium carbonate, ammonium cyanide, ammonium citrate, ammonium nitrate, calcium chloride, calcium acetate, calcium sulfate, calcium phosphate, calcium carbonate, calcium cyanide, calcium citrate, and calcium nitrate.

More preferably, the salt may be selected from the group consisting of sodium chloride, sodium acetate, sodium sulfate, sodium phosphate, and potassium chloride.

Preferably, the salt may be added at a final concentration of 0.1 to 3.0 M.

More preferably, the salt may be added at a final concentration of 0.3 to 2.5 M.

Preferably, if the salt is sodium chloride, it may be added at a final concentration of less than 3.0 M, if the salt is sodium acetate, it may be added at a final concentration of less than 2.5 M, if the salt is sodium sulfate, it may be added at a final concentration of less than 0.7 M, if the salt is sodium phosphate, it may be added at a final concentration of less than 0.8 M, or if the salt is potassium chloride, it may be added at a final concentration of 1.0 M or less.

Preferably, the reaction time of step (2) may be 4 to 18 hours.

Preferably, the reaction temperature of step (2) may be 0 to 25° C.

Preferably, if the non-peptidyl polymer has one or more aldehyde derivative as functional groups, the reaction mixture further comprises a reducing agent at a final concentration of 1 to 100 mM.

Preferably, step (1) may be performed at pH 5.0 to 6.5, and step (2) may be performed at pH 6.0 to 8.5.

Preferably, in step (1), the non-peptidyl polymer may react with the physiologically active polypeptide, and in step (2), the reaction mixture of step (1) may react with the immunoglobulin constant region.

Preferably, in step (1), the physiologically active polypeptide and the non-peptidyl polymer may react with each other at a molar ratio of 1:1 to 1:20, and in step (2), the product of step (1) and the immunoglobulin constant region may react with each other at a molar ratio of 1:0.5 to 1:10.

More preferably, step (2) may be carried out in the presence of sodium chloride added at a final concentration of less than 3.0 M, sodium acetate added at a final concentration of less than 2.5 M, sodium sulfate added at a final concentration of less than 0.7 M, sodium phosphate added at a final concentration of less than 0.8 M, or potassium chloride added at a final concentration of 1.0 M or less.

Preferably, the functional groups of the non-peptidyl polymer may be linked to an amine group which is present at an N-terminus or on a side chain of Lys residue of the physiologically active polypeptide and the immunoglobulin constant region.

Preferably, the non-peptidyl polymer may be selected from the group consisting of polyethylene glycols, polypropylene glycols, copolymers of ethylene glycol and propylene glycol, polyoxyethylated polyols, polyvinyl alcohols, polysaccharides, dextrans, polyvinyl ethyl ethers, polylactic acid (PLA), polylactic-glycolic acid (PLGA), lipid polymers, chitins, hyaluronic acid, and the combination thereof.

More preferably, the non-peptidyl polymer may be polyethylene glycol.

Preferably, the non-peptidyl polymer may have a molecular weight ranging from 1 to 100 kDa.

Preferably, the immunoglobulin constant region may be aglycosylated.

Preferably, the immunoglobulin constant region may consist of one to four domains selected from the group consisting of CH1, CH2, CH3 and CH4 domains.

Preferably, the immunoglobulin constant region may further include a hinge region.

Preferably, the immunoglobulin constant region may be selected from the group consisting of constant regions derived from IgG, IgA, IgD, IgE, IgM, combinations thereof, and hybrids thereof.

Preferably, the immunoglobulin constant region may be selected from the group consisting of constant regions of IgG1, IgG2, IgG3, IgG4, combinations thereof, and hybrids thereof.

More preferably, the immunoglobulin constant region may be an IgG4 Fc region.

Much more preferably, the immunoglobulin constant region may be an aglycosylated human IgG4 Fc region.

Preferably, the physiologically active polypeptide may be selected from the group consisting of human growth hormone, growth hormone releasing hormones, growth hormone releasing peptides, interferon, interferon receptors, colony-stimulating factors, glucagon-like peptides (GLP-1, etc.), oxyntomodulin, G protein-coupled receptors, interleukins, interleukin receptors, enzymes, interleukin-binding proteins, cytokine-binding proteins, macrophage activating factors, macrophage peptides, B-cell factors, T-cell factors, Protein A, allergy inhibitors, cell necrosis glycoproteins, immunotoxins, lymphotoxins, tumor necrosis factor, tumor suppressors, transforming growth factor, alpha-1 antitrypsin, albumin, α-lactalbumin, apolipoprotein-E, erythropoietin, glycosylated erythropoietin, angiopoeitins, hemoglobin, thrombin, thrombin receptor activating peptides, thrombomodulin, blood factor VII, VIIa, VIII, IX and XIII, plasminogen activators, fibrin-binding peptides, urokinase, streptokinase, hirudin, Protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, cell surface antigens, virus-derived vaccine antigens, monoclonal antibodies, polyclonal antibodies, and antibody fragments.

More preferably, the physiologically active polypeptide may be insulin.

Preferably, in step (1), the physiologically active polypeptide and the non-peptidyl polymer may be reacted with each other at a molar ratio of 1:1 to 1:20 under the pH condition of 5.0 to 6.5, and in step (2), the reaction mixture of step (1) and the immunoglobulin constant region may be reacted with each other at a molar ratio of 1:0.5 to 1:10 under the pH condition of 6.0 to 8.5 in the presence of the salt, in which if the salt is sodium chloride, it may be added at a final concentration of less than 3.0 M, if the salt is sodium acetate, it may be added at a final concentration of less than 2.5 M, if the salt is sodium sulfate, it may be added at a final concentration of less than 0.7 M, if the salt is sodium phosphate, it may be added at a final concentration of less than 0.8 M, or if the salt is potassium chloride, it may be added at a final concentration of 1.0 M or less.

Effect of the Invention

A conjugate of physiologically active polypeptide-non-peptidyl polymer-immunoglobulin constant region can be produced at high purity and yield by the preparation method of the present invention. Due to the method used to prepare the conjugate of the physiologically active polypeptide, production costs can be reduced thereby improving industrial applicability and drug compliance. Therefore, the method can be used to develop long-acting formulations of physiologically active polypeptides.

BRIEF DESCRIPTION OF THE DRAWINGS

FIG. 1 is a profile showing the result of purifying coupling reaction solutions of Examples 2 and 3 by Source 15Q column, in which contents of unreacted immunoglobulin Fc, a long-acting insulin conjugate (insulin-PEG-immunoglobulin Fc fragment conjugate) and impurities can be compared.

DETAILED DESCRIPTION OF THE PREFERRED EMBODIMENTS

In one aspect to achieve the above objects, the present invention provides a method for preparing a conjugate of physiologically active polypeptide-non-peptidyl polymer-immunoglobulin constant region, comprising the steps of: (1) reacting a non-peptidyl polymer with one of a physiologically active polypeptide or an immunoglobulin constant region; and (2) reacting the reaction mixture of step (1) with the other of the physiologically active polypeptide or the immunoglobulin constant region in the presence of a salt.

Step (1) is a step of linking the physiologically active polypeptide or the immunoglobulin constant region to the non-peptidyl polymer, and a known method used for linking the non-peptidyl polymer with the physiologically active polypeptide or the immunoglobulin constant region may be used. For example, it may be achieved by reacting them at 0 to 25° C. for 1 to 16 hours. Preferably, one non-peptidyl polymer can be covalently bonded to the physiologically active polypeptide or the immunoglobulin constant region through the functional group by the reaction to form a covalent bond. At this time, according to the type of the functional group participating in the reaction, a reducing agent can be further included at a concentration of 1 to 20 mM to carry out the reaction.

The non-peptidyl polymer may be linked to the physiologically active polypeptide and the immunoglobulin constant region via the functional groups included therein forming covalent bonds. Preferably, the functional groups of the non-peptidyl polymer can be linked to an amine group which is present at an N-terminus or on a side chain of Lys residue of the physiologically active polypeptide and the immunoglobulin constant region. In this regard, the position of Lys residue on the physiologically active polypeptide and the immunoglobulin constant region is not particularly limited to the specific site. The Lys residue is not limited to natural Lys, and non-natural amino acids and Lys derivatives are included without limitation, as long as they contain amine groups to be linked to the functional groups of the non-peptidyl polymer.

The reaction mixture may include the reaction products, such as a complex of the non-peptidyl polymer and the physiologically active polypeptide or a complex of the non-peptidyl polymer and the immunoglobulin constant region, and an unreacted reaction mixture. Therefore, the step of separating the complex of physiologically active polypeptide-non-peptidyl polymer or the complex of immunoglobulin constant region-non-peptidyl polymer from the reaction mixture may be further comprised after step (1).

The term "non-peptidyl polymer", as used herein, refers to a biocompatible polymer composed of two or more repeating units which are held together by a random covalent bond other than a peptide bond. Examples of the non-peptidyl polymer useful in the present invention include polyethylene glycols, polypropylene glycols, copolymers of ethylene glycol and propylene glycol, polyoxyethylated polyols, polyvinyl alcohols, polysaccharides, dextrans, polyvinyl ethyl ethers, biodegradable polymers such as polylactic acid (PLA) and polylactic-glycolic acid (PLGA), lipid polymers, chitins, hyaluronic acid and combinations thereof, with a preference for polyethylene glycol (PEG). The derivatives thereof that are well known in the art and derivatives which can be readily prepared using methods known in the art are also within the scope of the present invention.

Peptide linkers used in the fusion protein prepared according to the prior inframe fusion method have the disadvantage that they are easily cleaved in vivo by proteolytic enzymes, and therefore, any increase of the blood half-life of active drugs due to use of the corresponding carrier falls short of expectation. However, in the present invention, the blood half-life of the peptide is found to be similar to that of the carrier, due to using polymers which are resistant to proteolytic enzymes. Therefore, in the present invention, any polymer having the above function, i.e. having a resistance to in vivo proteolytic enzyme can be used as the non-peptide polymer without any limitation. The non-peptide polymers have a molecular weight in the range of 1 to 100 kDa, and preferably in the range of 1 to 20 kDa. In addition, the non-peptide polymer of the present invention, to be conjugated with the physiologically active polypeptide, may be not only one kind of polymer but also the combination of different kinds of polymers.

The non-peptide polymers as used in the present invention have the functional groups which can be conjugated with the immunoglobulin Fc region and the protein drug.

Preferably, the non-peptidyl polymer may be linked to an amine group or thiol group on a side chain of amino acid residue of the physiologically active polypeptide to form a peptide, hemithioacetal, imine, or thiodioxopyrrolidinyl bond.

Non-limiting example of the terminal functional groups of the non-peptide polymers may include aldehyde derivatives such as a propionaldehyde group and a butyraldehyde group, maleimide derivatives, and succinimide derivatives. The succinimide derivatives may include succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate, but are not limited thereto. The functional groups that can be selectively linked to the amine group or thiol group of amino acid residue of the immunoglobulin Fc region and the physiologically active polypeptide so as to form a covalent bond may be used without limitation.

The functional groups at both ends of the non-peptidyl polymer may be the same as or different from each other. For example, the non-peptide polymer may possess a succinimide group at one end, and an aldehyde derivative such as a propionaldehyde group or a butyraldehyde group at the other end. When polyethylene glycol having a reactive hydroxy group at both ends thereof is used as the non-peptidyl polymer, the hydroxy group may be activated to various functional groups by known chemical reactions, or commercially available polyethylene glycol having a modified functional group may be used so as to prepare the protein conjugate of the present invention.

Preferably, the non-peptidyl polymer may have propionaldehyde groups as functional groups at both ends.

Conjugation with PEG, which is typically used to prepare long-acting protein formulations, increases the stability of the proteins, while larger molecular weights of PEG exhibit lower reactivity with the proteins and thus decrease the production yield. Since the production yield is closely correlated with production cost and the corresponding industrial applicability, it is very important to increase the production yield. PEG with aldehyde functional groups may be coupled to an amine group, which is present at an N-terminus or on the R group of Lys residue of the polypeptide. The yield of PEGylation may vary depending on the molar ratio of PEG to proteins, the concentration of reaction solutions, the time of reaction, pH, temperature, etc.

However, when a non-peptidyl polymer including PEG with two or more functional groups is used as a linker between two different polypeptides, two or more steps in reactions are required, thus lowering the overall yield. Particularly, a step of the second reaction (wherein the physiologically active polypeptide or immunoglobulin constant region conjugated with a non-peptidyl polymer having two or more functional groups reacts with the immunoglobulin constant region or the physiologically active polypeptide, respectively, hereinafter referred as "coupling reaction") was observed to be conducted with a significantly lower yield, compared to a step of the first reaction in which the physiologically active polypeptide or the immunoglobulin constant region reacts with a non-peptidyl polymer having two or more functional groups.

The present inventors found a correlation between salt addition during the coupling reaction and reaction yield, and they confirmed that the coupling reaction yield is improved by using a salt.

The salt in the present invention is an ionic compound that has a neutral net charge, resulting from the formation of electrical bonds between equal numbers of anions and cations (considering ionic valence), and dissociates into cations and anions in an aqueous solution. With respect to the objects of the present invention, the salt may be added to the reaction solution so that the complex of the non-peptidyl polymer and the physiologically active polypeptide or the complex of the non-peptidyl polymer and the immunoglobulin constant region is linked to the immunoglobulin constant region or the physiologically active polypeptide to form a covalent bond. Common salt-forming cations include ammonium ($NH_4^+$), calcium ($Ca^{2+}$), iron ($Fe^{2+}$ or $Fe^{3+}$), magnesium ($Mg^{2+}$), potassium ($K^+$), pyridinium ($C_5H_5NH^+$), quaternary ammonium ($NR_4^+$) or sodium ($Na^+$), and anions may include acetate ($CH_3COO-$), carbonate ($CO_3^{2-}$), chloride ($Cl^-$), citrate ($HOC(COO-)(CH_2COO^-)_2$), cyanide ($CN^-$), nitrate ($NO_3^-$), nitrite ($NO_2^-$), phosphate ($PO_4^{3-}$) or sulfate ($SO_4^{2-}$). The salt may be formed in combinations of the above described cations and anions. The salt may be a salt typically used in the art, but is not limited to, preferably sodium chloride, sodium acetate, sodium sulfate, sodium phosphate, sodium carbonate, sodium cyanide, sodium citrate, sodium nitrate, potassium chloride, potassium acetate, potassium sulfate, potassium phosphate, potassium carbonate, potassium cyanide, potassium citrate, potassium nitrate, magnesium chloride, magnesium acetate, magnesium sulfate, magnesium phosphate, magnesium carbonate, magnesium cyanide, magnesium citrate, magnesium nitrate, ammonium chloride, ammonium acetate, ammonium sulfate, ammonium phosphate, ammonium carbonate, ammonium cyanide, ammonium citrate, ammonium nitrate, calcium chloride, calcium acetate, calcium sulfate, calcium phosphate, calcium carbonate, calcium cyanide, calcium citrate, or calcium nitrate. More preferably, the salt may be sodium chloride, sodium acetate, sodium sulfate, sodium phosphate, or potassium chloride. As the salt, a proper salt may be freely selected depending on the type of the physiologically active polypeptide and the reaction solvent.

The salt may be included in the reaction solution so that the non-peptidyl polymer linked to the physiologically active polypeptide or the immunoglobulin constant region via one functional group is effectively linked to the immunoglobulin constant region or the physiologically active polypeptide via the other functional group. In order to increase the coupling reaction yield of the non-peptidyl polymer, the final concentration of the salt may be relatively high, for example, less than 3.0 M. The lower concentration limit of the salt may be determined by repeating experiments, and as a proper range of the salt concentration, for example, it can be suggested that the salt is included at a final concentration of 0.1 to 3 M, and more specifically, at a final concentration of 0.3 to 2.5 M during coupling reaction.

Preferably, if the salt is sodium chloride, it may be added at a final concentration of less than 3.0 M, if the salt is sodium acetate, it may be added at a final concentration of less than 2.5 M, if the salt is sodium sulfate, it may be added at a final concentration of less than 0.7 M, if the salt is sodium phosphate, it may be added at a final concentration of less than 0.8 M, or if the salt is potassium chloride, it may be added at a final concentration of 1.0 M or less. If the salt concentration exceeds the above range according to the type of the salt, the yield increases, but agglomeration may occur, undesirably. Although agglomeration occurs, it is possible to prepare the conjugates, but difficulties in the process are created. In terms of process convenience, therefore, it is preferable that the salt is added at a concentration not to cause excessive agglomeration, that is, to generate no agglomeration or a trace amount of agglomerates. For example, when addition of the salt during the coupling reaction increases the overall yield compared to before addition of the salt in spite of agglomeration, such agglomeration is acceptable as long as it does not cause serious problems in separation and/or purification.

In a specific embodiment of the present invention, when a conjugate was prepared by linking insulin, a PEG linker containing two aldehyde groups as functional groups, and the immunoglobulin constant region, the reaction was allowed to proceed by using a salt under various conditions in order to increase the yield. It was found that use of the salt during the coupling reaction improves the yield (Table 1). Further, the present inventors found that improvement of the coupling reaction yield by addition of the salt can be achieved by preventing generation of impurities due to side reaction, for example, by preventing generation of multimers that can be formed by binding two different complexes of insulin-PEG to two N-terminals of one immunoglobulin constant region (FIG. 1).

In the present invention, the coupling reaction, that is, the reaction of step (2) may be preferably carried out for 4 to 18 hours. In addition, the coupling reaction may be carried out at 0 to 25° C. However, the reaction condition is not limited thereto.

In the present invention, if the non-peptidyl polymer has one or more aldehyde derivatives as functional groups, the reaction mixture may further comprise a reducing agent at a final concentration of 1 to 100 mM.

In the present invention, the reducing agent means a compound that functions to reduce the reversible imine double bond formed from a reaction between the aldehyde group of the non-peptidyl polymer and the amine group of the polypeptides (physiologically active polypeptide, immunoglobulin constant region), thereby forming a covalent bond, and is intended to encompass all reducing agents known in the art. With respect to the objects of the present invention, the reducing agent may be added to the reaction solution in which the non-peptidyl polymer forms a covalent bond with the physiologically active polypeptide or the immunoglobulin constant region. As long as it is typically used in the art, any reducing agent may be employed in the present invention. Preferably, examples of the reducing agent may include, but are not limited to, sodium cyanoborohydride, borane pyridine complex, sodium borohydride, borane dimethylamine complex, borane trimethylamine complex or sodium triacetoxyborohydride. An adequate reducing agent may be freely selected depending on the types of the physiologically active polypeptide or the immunoglobulin constant region and the reaction solvent.

The reducing agent is included in the reaction solution for conjugation of the physiologically active polypeptide or the immunoglobulin constant region with the non-peptidyl polymer. The reducing agent may be included at a concentration of 1-20 mM for the reaction between the physiologically active polypeptide and the non-peptidyl polymer or the immunoglobulin constant region and the non-peptidyl polymer (reaction of step (1)), and at a concentration of 1100 mM for the coupling reaction (reaction of step (2)).

Preferably, step (1) may be carried out at pH 5.0 to 6.5 and step (2) may be carried out at pH 6.0 to 8.5. Further, the reaction may be carried out under conditions, in which ionic strength is controlled within 20 to 500 mM using sodium citrate and potassium phosphate or HEPES, but is not limited thereto.

In a specific embodiment of the present invention, PEG having propionaldehydes as functional groups at both ends thereof was used as the non-peptidyl polymer and reacted with insulin as the physiologically active polypeptide to prepare a complex of PEG-insulin, and then coupling reaction with the immunoglobulin constant region was carried out in the presence of the salt to prepare a conjugate of insulin-PEG-immunoglobulin constant region.

As described above, the linkage with the non-peptidyl polymer occurs between the functional groups of the non-peptidyl polymer and an amine group which is present at an N-terminus of the physiologically active polypeptide or the immunoglobulin constant region or an amine group or a thiol group on a side chain of amino acid residue constituting them. Meanwhile, because the immunoglobulin constant region has two N-terminals, one immunoglobulin constant region is linked through two functional groups on the same non-peptidyl polymer molecule, or through functional groups on two different non-peptidyl polymer molecules. However, the conjugate formed by the preparation method according to the present invention is preferably in the form in which each one molecule of the physiologically active polypeptide, the non-peptidyl polymer and the immunoglobulin constant region is linked to each other, that is, one molecule of the physiologically active polypeptide and one molecule of the immunoglobulin constant region are linked to both ends of immunoglobulin constant region is linked to two functional groups of the same non-peptidyl polymer molecule, all the functional groups at both ends of the non-peptidyl polymer are linked to the immunoglobulin constant regions, and thus they cannot be linked to the physiologically active polypeptide by coupling reaction. When one immunoglobulin constant region is linked to each of the functional groups of two different non-peptidyl polymer molecules, multimers may be formed in the form of pseudo dimer.

Therefore, in one embodiment of the present invention, in step (1), the non-peptidyl polymer reacts with the physiologically active polypeptide, and in step (2), the reaction mixture of step (1) reacts with the immunoglobulin constant region. If the non-peptidyl polymer first reacts with the physiologically active polypeptide to form a complex of physiologically active polypeptide-non-peptidyl polymer, and then the complex reacts with the immunoglobulin constant region by coupling reaction, it can prevent a complex from being formed by linking one immunoglobulin constant region to both ends of one non-peptidyl polymer, which may occur when the immunoglobulin constant region and the non-peptidyl polymer are first reacted.

In a specific example of the above embodiment, it is preferable that in step (1), the physiologically active polypeptide and the non-peptidyl polymer are reacted at a molar ratio of 1:1 to 1:20, and in step (2), the complex of the physiologically active polypeptide and the non-peptidyl polymer as a product of step (1) and the immunoglobulin constant region are reacted at a molar ratio of 1:0.5 to 1:10, but is not limited thereto.

More specifically, step (2) may be carried out by adding sodium chloride at a final concentration of less than 3.0 M, sodium acetate at a final concentration of less than 2.5 M, sodium sulfate at a final concentration of less than 0.7 M, sodium phosphate at a final concentration of less than 0.8 M, or potassium chloride at a final concentration of 1.0 M or less, but is not limited to the type and concentration of the salt. As long as agglomeration excessive enough to interfere with the process in the reaction mixture is not generated, various types of salt can be added at different concentrations. The salt can be used at a concentration which causes agglomeration corresponding to the agglomeration level regarded as acceptable when no salt is added.

More specifically, step (1) is a step of reacting the physiologically active polypeptide with the non-peptidyl polymer at a molar ratio of 1:1 to 1:20 under pH condition of 5.0 to 6.5, and step (2) is a step of reacting the reaction mixture of step (1) with the immunoglobulin constant region at a molar ratio of 1:0.5 to 1:10 under pH condition of 6.0 to 8.5 in the presence of the salt, and if the salt is sodium chloride, it may be added at a final concentration of less than 3.0 M, if the salt is sodium acetate, it may be added at a final concentration of less than 2.5 M, if the salt is sodium sulfate, it may be added at a final concentration of less than 0.7 M, if the salt is sodium phosphate, it may be added at a final concentration of less than 0.8 M, or if the salt is potassium chloride, it may be added at a final concentration of 1.0 M or less.

Step (1) is a reaction for preparing the complex of physiologically active polypeptide-non-peptidyl polymer, and thereafter, a step of purifying the product may be further carried out. Step (2) is a reaction for preparing the conjugate of physiologically active polypeptide-non-peptidyl polymer-immunoglobulin constant region by reacting the complex of physiologically active polypeptide-non-peptidyl polymer as the product of step (1) with the immunoglobulin constant region. The conjugate can be prepared with improved yield by controlling the reaction conditions and the molar ratio of the reactants as described above.

As used herein, the term "physiologically active polypeptide" refers a polypeptide having a certain physiological function in vivo as a general concept. It has a polypeptidyl structure in common and shows various biological activities. When the body becomes biologically abnormal as a result of a lack or an excessive secretion of a material involved in a certain function, the physiologically active polypeptide may regulate the genetic expression or physiological function, thereby correcting the abnormality. Typical protein drugs may be included.

The physiologically active polypeptide may be selected from the group consisting of human growth hormone, growth hormone releasing hormones, growth hormone releasing peptides, interferon, interferon receptors, colony-stimulating factors, glucagon-like peptides (GLP-1, etc.), oxyntomodulin, G protein-coupled receptors, interleukins, interleukin receptors, enzymes, interleukin-binding proteins, cytokine-binding proteins, macrophage activating factors, macrophage peptides, B-cell factors, T-cell factors, Protein A, allergy inhibitors, cell necrosis glycoproteins, immuno-toxins, lymphotoxins, tumor necrosis factor, tumor suppressors, transforming growth factor, alpha-1 anti-trypsin, albumin, α-lactalbumin, apolipoprotein-E, erythropoietin, glycosylated erythropoietin, angiopoeitins, hemoglobin, thrombin, thrombin receptor activating peptides, thrombomodulin, blood factor VII, VIIa, VIII, IX and XIII, plasminogen activators, fibrin-binding peptides, urokinase, streptokinase, hirudin, Protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, cell surface antigens, virus-derived vaccine antigens, monoclonal antibodies, polyclonal antibodies, and antibody fragments. Preferably, the physiologically active polypeptide may be insulin, but is not limited thereto.

Insulin used in the embodiment of the present invention is a kind of physiologically active peptides secreted from the pancreas when blood glucose level becomes high, which functions to control blood glucose levels by causing the liver, skeletal muscles, and fat tissue to take up glucose from the blood and store it as glycogen, and by suppressing lipolysis, a metabolism for using fat as an energy source. In terms of the structure, insulin comprises alpha chain and beta chain. The terms of insulin alpha chain and insulin beta chain can be used interchangeably with insulin A chain and insulin B chain, respectively. These peptides include insulin agonists, precursors, derivatives, fragments, and variants. Native insulin, fast-acting insulin, and long-acting insulin are preferred.

Native insulin is a hormone secreted from the pancreas and plays a critical role in the control of blood glucose levels by promoting the cellular uptake of glucose and inhibiting lipolysis. Insulin having a function of regulating blood glucose levels is produced from a proinsulin precursor without a function of regulating blood glucose levels, through a series of the processes. The amino acid sequence of insulin is as follows:

```
Alpha chain:
                                         (SEQ ID NO. 1)
Gly-Ile-Val-Glu-Gln-Cys-Cys-Thr-Ser-Ile-Cys-Ser- Leu-Tyr-Gln-Leu-Glu-Asn-Tyr-Cys-Asn Beta chain:
                                         (SEQ ID NO. 2)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

Insulin agonists mean the substance which binds to the in vivo insulin receptor and exhibits the same biological activities as that of insulin regardless of the structure of insulin.

Insulin derivatives denote a peptide which shows a sequence homology of at least 80% in an amino acid sequence as compared to native insulin, has some groups of amino acid residues altered in the form of chemical substitution (e.g. alpha-methylation, alpha-hydroxylation), removal (e.g. deamination) or modification (e.g. N-methylation, glycosylation, fatty acid), and has a function of controlling blood glucose level in the body.

Insulin fragments denote the type of insulin in which one or more amino acids are added to, or deleted from, amino or carboxy terminals of insulin, and the amino acids as added can also be non-native amino acids (e.g. D type amino acid). Such insulin fragments retain the function of controlling blood glucose level in the body.

Insulin variants denote a peptide which differs from insulin in one or more in the amino acid sequence, and retains the function of controlling blood glucose level in the body.

The respective methods used for preparation of insulin agonists, derivatives, fragments and variants can be employed independently or in combination. For example, the insulin peptide may include peptides of which one or more in the amino acid sequence differ from those of native insulin and which have deamination at N-terminal amino acid residue, having the function of controlling blood glucose level in the body.

As used herein, the term "immunoglobulin constant region" refers to an immunoglobulin fragment that is devoid of the variable regions of light and heavy chains, the constant region 1 of the heavy chain (CH1), and the constant region of the light chain (CL), that is, an Fc region comprised of the constant regions 2 and 3 of the heavy chain (CH2 and CH3) (or inclusive of the constant region of the heavy chain (CH4)). Optionally, the immunoglobulin Fc region may further comprise a hinge region. Also, the immunoglobulin constant region of the present invention may be an extended immunoglobulin Fc region which comprises a part of or the entirety of the constant region 1 of the heavy chain (CH1) and/or the constant region of the light chain (CL) except only for the variable regions of heavy and light chains of the immunoglobulin so long as it shows effects substantially identical or superior to those of the native immunoglobulin constant region. Further, the immunoglobulin constant region of the present invention may be lack of a significant part of the amino acid sequence which corresponds to CH2 and/or CH3. Consequently, the immunoglobulin constant region of the present invention may comprise (1) CH1 domain, CH2 domain, CH3 domain and CH4 domain, (2) CH1 domain and CH2 domain, (3) CH1 domain and CH3 domain, (4) CH2 domain and CH3 domain, (5) a combination of one or more constant domains and an immunoglobulin hinge region (or a partial hinge region), or (6) a dimer of each constant domain of the heavy chain and the constant region of the light chain.

An immunoglobulin constant region including Fc region is a biodegradable polypeptide which can be metabolized in vivo, so that it can safely be used as a drug carrier. In addition, an immunoglobulin Fc region is more advantageous in terms of production, purification and production yield of a conjugate than an entire immunoglobulin molecule owing to its relatively lower molecular weight. Further, since it is devoid of Fab, which exhibits high non-homogeneity due to the difference in amino acid sequence from one antibody to another, the immunoglobulin Fc alone provides the conjugate with significantly enhanced homogeneity, and reduces the possibility of inducing blood antigenicity.

On the other hand, the immunoglobulin constant region may originate from humans or animals, such as cows, goats, pigs, mice, rabbits, hamsters, rats, guinea pigs, etc., and may be preferably of human origin. In addition, the immunoglobulin constant region may be selected from Fc fragments derived from IgG, IgA, IgD, IgE, IgM, or combinations or hybrids thereof. Preferably, the constant region is derived from IgG or IgM, which are the most abundant ones in blood, and most preferably from IgG, which is known to improve the serum half life of ligand-binding proteins.

As used herein, the term "combination" means that polypeptides encoding single-chain immunoglobulin constant regions (preferably Fc regions) of the same origin are linked to a single-chain polypeptide of a different origin to form a dimer or multimer. That is, a dimer or a multimer may be prepared by combination of two or more fragments selected from the group consisting of fragments of IgG Fc, IgA Fc, IgM Fc, IgD Fc and IgE.

As used herein, the term "hybrid" means that sequences encoding two or more immunoglobulin constant regions of different origins are present in a single-chain of immunoglobulin constant region (preferably, an Fc region). In the present invention, various hybrid forms are possible. For example, the hybrid domain can be composed of one to four domains selected from the group consisting of CH1, CH2, CH3 and CH4 of IgG Fc, IgM Fc, IgA Fc, IgE Fc and IgD Fc, and may include a hinge region.

IgG is divided into the IgG1, IgG2, IgG3 and IgG4 subclasses, and the present invention may include combinations or hybrids thereof. Preferred are the IgG2 and IgG4 subclasses, and most preferred is the Fc region of IgG4 rarely having effector functions such as Complement Dependent Cytotoxicity (CDC).

The immunoglobulin constant region may be in the form of having native sugar chains, increased sugar chains or decreased sugar chains compared to the native form, or may be in a deglycosylated form. The increase, decrease or removal of sugar chains of the immunoglobulin constant region may be achieved by typical methods in the art, such as a chemical method, an enzymatic method and a genetic engineering method using a microorganism. Here, the deglycosylated immunoglobulin constant region shows a sharp decrease in binding affinity to the complement (c1q) and decrease or loss in antibody-dependent cytotoxicity or complement-dependent cytotoxicity, thereby not inducing unnecessary immune responses in-vivo. In this regard, an immunoglobulin constant region in a deglycosylated or aglycosylated form may be more suitable to the object of the present invention as a drug carrier. Accordingly, a human IgG4-derived aglycosylated Fc region may be much more preferably used. The human-derived Fc region is more preferable than a non-human derived Fc region, which may act as an antigen in the human body and cause undesirable immune responses such as the production of a new antibody against the antigen.

Further, not only the immunoglobulin constant region with the native amino acid sequence but also its amino acid sequence mutant may be included within the scope of the immunoglobulin constant region of the present invention. An amino acid sequence derivative has a sequence that differs in one or more amino acid residues from the native amino acid sequence due to a deletion, an insertion, a non-conservative or conservative substitution or combinations thereof. For example, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used in the present invention. In addition, complement fixation sites, e.g., C1q fixation sites, or ADCC sites may be eliminated from the native Fc region to remove the effector function. The techniques of preparing amino acid sequence mutants of the immunoglobulin constant region are disclosed in International Patent Publication Nos. WO 97/34631 and WO 96/32478.

Amino acid substitutions in proteins and peptides, which do not generally alter the activity of molecules, are well known in the art (H. Neurath, R. L. Hill, The Proteins, Academic Press, New York, 1979). The most common substitutions occur between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, Asp/Gly. Optionally, amino acids may be modified by phosphorylation, sulfation, acrylation, glycosylation, methylation, farnesylation, acetylation, and amidation.

The aforementioned immunoglobulin constant region derivatives may be derivatives exhibiting the same biological activity as that of the immunoglobulin constant region of the present invention meanwhile having improved structural stability against heat, pH, or the like. In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Here, they may be obtained from a native immunoglobulin by isolating whole immunoglobulins from human or animal organisms and treating them with a proteolytic enzyme. Immunoglobulins are cleaved into Fab and Fc regions by Papain treatment, and into pF'c and F(ab)$_2$ by pepsin treatment. These fragments may be subjected to size-exclusion chromatography to isolate Fc or pF'c.

Preferably, a human-derived immunoglobulin constant region may be a recombinant immunoglobulin constant region that is obtained from a microorganism.

Hereinafter, the present invention will be described in more detail with reference to the following Examples. However, these Examples are for illustrative purposes only, and the invention is not intended to be limited by these Examples.

Example 1: PEGylation Reaction of Insulin and Purification of Mono-Pegylated Insulin Insulin powder was dissolved in 10 mM HCl, and then reacted with 3.4K propion-ALD2 PEG (PEG having two propionaldehyde groups at both ends, IDB, Korea) at 4° C. for about 2 hours at a molar ratio of 1:4 of insulin:PEG and an insulin concentration of 5 mg/ml to pegylate the N-terminal of the insulin beta chain. This reaction was conducted under 50 mM sodium citrate pH 6.0, in 45% isopropanol with addition of 3.0 mM sodium cyanoborohydride, a reducing agent. The reaction solution was purified with SP-HP (GE Healthcare) column using a buffer containing sodium citrate (pH 3.0) and 45% EtOH, and a KCl concentration gradient.

Example 2: Preparation of Conjugate by Coupling Reaction without Salt Addition

To prepare a conjugate of insulin-PEG-immunoglobulin Fc fragment, mono-PEGylated insulin prepared by the method of Example 1 and an immunoglobulin Fc fragment were reacted at a molar ratio of 1:1.2 with a total protein level of 20 mg/ml at 25° C. for 13 hours. At this time, the reaction solution contained 100 mM HEPES, 22 mM potassium phosphate, and 10% ethanol at pH 8.2, and further contained 20 mM sodium cyanoborohydride as a reducing agent.

After completion of the reaction, the reaction solution was passed through Source 15Q (GE Healthcare) column to separate and purify the unreacted insulin, the unreacted immunoglobulin Fc fragment, the conjugate of insulin-PEG-immunoglobulin Fc fragment, and the conjugate of immunoglobulin Fc fragment coupled with two or more mono-PEGylated insulin (insulin-PEG) using Tris-HCl (pH 7.5) buffer and a NaCl concentration gradient. In this regard, the content of impurities was identified on a profile (FIG.

Then, Source 15ISO (GE Healthcare) was used as a second column to remove any residual immunoglobulin Fc and multi-coupled insulin conjugate, thereby obtaining the conjugate of insulin-PEG-immunoglobulin Fc. In this case, the elution was conducted using a concentration gradient of ammonium sulfate containing Tris-HCl (pH 7.5). The eluted conjugate of insulin-PEG-immunoglobulin Fc was analyzed with RP-HPLC and IE-HPLC.

Example 3: Improvement of Coupling Reaction Yield by Addition of Sodium Chloride To examine the effect of sodium chloride on the coupling reaction yield, mono-PEGylated insulin prepared by the method of Example 1 and the immunoglobulin Fc fragment were reacted at a molar ratio of 1:1.2 with a total protein level of 20 mg/ml at 25° C. for 13 hours. At this time, the reaction solution contained 100 mM HEPES, 22 mM potassium phosphate, and 10% ethanol at pH 8.2 with addition of sodium chloride to a final concentration of 0.5 to 3.0 M, and further contained 20 mM sodium cyanoborohydride as a reducing agent.

The reaction solution was purified and analyzed in the same manner as in Example 2. The addition of sodium chloride to the coupling solution improved the coupling reaction yield, compared to no addition. This effect was maximized by addition of sodium chloride with a final concentration of 2.0 M (Table 1). The results of Source 15Q profile showed that impurities due to a side reaction were decreased as the yield was improved (FIG. 1). It was also confirmed that when the coupling reaction was conducted by addition of 2.0 M sodium chloride, highly pure conjugate of insulin-PEG-immunoglobulin Fc with purity of 95% or more can be prepared (Table 2). In contrast, when sodium chloride was added at a final concentration of 3.0 M, agglomeration started to be observed.

Example 4: Improvement of Coupling Reaction Yield by Addition of Sodium Acetate

To examine the effect of sodium acetate on the coupling reaction yield, mono-PEGylated insulin prepared by the method of Example 1 and the immunoglobulin Fc fragment were reacted at a molar ratio of 1:1.2 with a total protein level of 20 mg/ml at 25° C. for 13 hours. At this time, the reaction solution contained 100 mM HEPES, 22 mM potassium phosphate, and 10% ethanol at pH 8.2 with addition of sodium acetate to a final concentration of 1.5 to 3.0 M, and further contained 20 mM sodium cyanoborohydride as a reducing agent.

The reaction solution was purified and analyzed in the same manner as in Example 2. The addition of sodium acetate to the coupling solution improved the coupling reaction yield, compared to no addition. This effect was maximized by addition of sodium acetate with a final concentration of 1.5 M (Table 1). It was also confirmed that when the coupling reaction was conducted by addition of 1.5 M sodium acetate, highly pure conjugate of insulin PEG immunoglobulin Fc with purity of 95% or more can be prepared (Table 2). In contrast, when sodium acetate was added at a final concentration of 2.5 M or higher, it is difficult to calculate the yield due to agglomeration.

Example 5: Improvement of Coupling Reaction Yield by Addition of Sodium Sulfate

To examine the effect of sodium sulfate on the coupling reaction yield, mono-PEGylated insulin prepared by the method of Example 1 and the immunoglobulin Fc fragment were reacted at a molar ratio of 1:1.2 with a total protein level of 20 mg/ml at 25° C. for 13 hours. At this time, the reaction solution contained 100 mM HEPES, 22 mM potassium phosphate, and 10% ethanol at pH 8.2 with addition of sodium sulfate to a final concentration of 0.4 to 0.7 M, and further contained 20 mM sodium cyanoborohydride as a reducing agent.

The reaction solution was purified and analyzed in the same manner as in Example 2. The addition of sodium sulfate to the coupling solution improved the coupling reaction yield, compared to no addition. This effect was maximized by addition of sodium sulfate with a final concentration of 0.4 M (Table 1). When sodium sulfate was added at a final concentration of 0.5 M, agglomeration started to be observed. When sodium sulfate was added at a final concentration of 0.7 M or higher, it is difficult to calculate the yield due to agglomeration.

Example 6: Improvement of Coupling Reaction Yield by Addition of Sodium Phosphate To examine the effect of sodium phosphate on the coupling reaction yield, mono-PEGylated insulin prepared by the method of Example 1 and the immunoglobulin Fc fragment were reacted at a molar ratio of 1:1.2 with a total protein level of 20 mg/ml at 25° C. for 13 hours. At this time, the reaction solution contained 100 mM HEPES, 22 mM potassium phosphate, and 10% ethanol at pH 8.2 with addition of sodium phosphate to a final concentration of 0.4 to 0.8 M, and further contained 20 mM sodium cyanoborohydride as a reducing agent.

The reaction solution was purified and analyzed in the same manner as in Example 2. The addition of sodium phosphate to the coupling solution improved the coupling reaction yield, compared to no addition. This effect was maximized by addition of sodium phosphate with a final concentration of 0.4 M (Table 1). In contrast, when sodium phosphate was added at a final concentration of 0.6 M, agglomeration started to be observed. When sodium sulfate was added at a final concentration of 0.8 M, it is difficult to calculate the yield due to agglomeration.

Example 7: Improvement of Coupling Reaction Yield by Addition of Potassium Chloride To examine the effect of potassium chloride on the coupling reaction yield, mono-PEGylated insulin prepared by the method of Example 1 and the immunoglobulin Fc fragment were reacted at a molar ratio of 1:1.2 with a total protein level of 20 mg/ml at 25° C. for 13 hours. At this time, the reaction solution contained 100 mM HEPES, 22 mM potassium phosphate, and 10% ethanol at pH 8.2 with addition of potassium chloride to a final concentration of 0.5 to 1.0 M, and further contained 20 mM sodium cyanoborohydride as a reducing agent.

The reaction solution was purified and analyzed in the same manner as in Example 2. The addition of potassium chloride to the coupling solution improved the coupling reaction yield, compared to no addition. This effect was maximized by addition of potassium chloride with a final concentration of 1.0 M (Table 1).

The following Table 1 shows the coupling reaction yield and the total yield according to the type and concentration of salt in the coupling reaction during preparation of the conjugate including insulin and the immunoglobulin Fc fragment.

TABLE 1

| Type of salt | Concentration (M) | Degree of agglomeration by visual examination | Coupling reaction yield (%) | Total yield (%) |
|---|---|---|---|---|
| No addition (control group) | — | − | 32.3 | 16.2 |
| Sodium chloride | 0.5 | − | 35.7 | 17.9 |
|  | 1.0 | − | 39.2 | 19.7 |
|  | 1.5 | − | 41.2 | 20.6 |
|  | 2.0 | − | 42.2 | 21.2 |
|  | 2.5 | − | 39.8 | 20.0 |
|  | 3.0 | + | 37.0 | 18.9 |
| Sodium acetate | 1.5 | − | 43.4 | 21.7 |
|  | 2.0 | − | 39.2 | 19.7 |
|  | 2.5 | +++ | — | — |
|  | 3.0 | ++++ | — | — |
| Sodium sulfate | 0.4 | − | 36.3 | 18.2 |
|  | 0.5 | + | 43.5 | 21.8 |
|  | 0.6 | + | 42.1 | 21.1 |
|  | 0.7 | +++ | — | — |
| Sodium phosphate | 0.4 | − | 40.7 | 20.4 |
|  | 0.6 | ++ | 39.2 | 19.7 |
|  | 0.8 | +++ | — | — |
| Potassium chloride | 0.5 | − | 35.2 | 17.6 |
|  | 1.0 | − | 35.8 | 17.9 |

−: no agglomeration, +: trace amount, ++; small amount, +++; excessive amount, ++++; full agglomeration As shown in Table 1, the salt-added groups showed increased coupling reaction yields of 35.2% to 43.5% from 32.3% and increased total yields of 17.6% to 21.8% from 16.2%, compared to the non-addition control group, although they differ depending on the type and concentration of the salt. Their rates of change with respect to the yield of the non-addition control group were converted, and rates of change of the coupling reaction yield and the total yield were as high as 9 to 35%.

The following Table 2 shows purity of the final conjugate that was prepared by adding 2.0 M sodium chloride or 1.5 M sodium acetate to the coupling reaction solution during preparation of the conjugate including insulin and immunoglobulin Fc fragment. Purity was double-checked by HPLC analysis using size exclusion chromatography (hereinafter, referred to as SE) and ion exchange chromatography (hereinafter, referred to as IE).

TABLE 2

| Salt | HPLC analysis result for purity of conjugate |
|---|---|
| 2.0M sodium chloride | SE 98.1%, IE 98.5% |
| 1.5M sodium acetate | SE 96.2%, IE 96.9% |

What is claimed is:

1. A method for preparing a conjugate of physiologically active polypeptide-non-peptidyl polymer-immunoglobulin constant region, comprising the steps of:
   (1) reacting a non-peptidyl polymer with a physiologically active polypeptide or an immunoglobulin constant region to form a complex of physiologically active polypeptide-non-peptidyl polymer or a complex of immunoglobulin constant region-non-peptidyl polymer; and
   (2) reacting the complex of physiologically active polypeptide-non-peptidyl polymer prepared in step (1) with an immunoglobulin constant region, or reacting the complex of immunoglobulin constant region-non-peptidyl polymer prepared in step (1) with a physiologically active polypeptide in the presence of a salt to form a conjugate of physiologically active polypeptide-non-peptidyl polymer-immunoglobulin constant region;
   wherein the non-peptidyl polymer is selected from the group consisting of polyethylene glycols, polypropylene glycols, copolymers of ethylene glycol and propylene glycol, polyoxyethylated polyols, polyvinyl alcohols, polysaccharides, dextrans, polyvinyl ethyl ethers, polylactic acid, polylactic-glycolic acid, lipid polymers, chitins, hyaluronic acid, and a combination thereof;
   wherein the salt is a chloride salt which is added at a final concentration of 0.5 to 2.5 M; an acetate salt which is added at a final concentration of 0.3 to 2.0 M; a sulfate salt which is added at a final concentration of 0.4 to 0.6 M; or a phosphate salt which is added at a final concentration of 0.4 to 0.6 M; and
   wherein the step (2) is carried out at pH 6.0 to 8.5.

2. The method according to claim 1, wherein the non-peptidyl polymer has each independently a functional group selected from the group consisting of an aldehyde derivative, a maleimide derivative and a succinimide derivative at both ends thereof.

3. The method according to claim 2, wherein the non-peptidyl polymer is linked to the physiologically active polypeptide and the immunoglobulin constant region via the functional groups at both ends thereof to form a covalent bond.

4. The method according to claim 1, further comprising the step of separating a complex of physiologically active polypeptide-non-peptidyl polymer or a complex of immunoglobulin constant region-non-peptidyl polymer from the reaction mixture after step (1).

5. The method according to claim 1, wherein the salt is selected from the group consisting of sodium chloride, sodium acetate, sodium sulfate, sodium phosphate and potassium chloride.

6. The method according to claim 5, wherein the salt is sodium chloride which is added at a final concentration of 0.5 to 2.5 M; sodium acetate which is added at a final concentration of 0.3 to 2.0 M; sodium sulfate which is added at a final concentration of 0.4 to 0.6 M; sodium phosphate which is added at a final concentration of 0.4 to 0.6 M; or potassium chloride which is added at a final concentration of 0.5 to 1.0 M.

7. The method according to claim 1, wherein the reaction time of step (2) is 4 to 18 hours.

8. The method according to claim 1, wherein the reaction temperature of step (2) is 0 to 25° C.

9. The method according to claim 1, wherein the non-peptidyl polymer has one or more aldehyde derivative as functional groups and the reaction solution further comprises a reducing agent at a final concentration of 1 to 100 mM.

10. The method according to claim 1, wherein step (1) is carried out at pH 5.0 to 6.5.

11. The method according to claim 1, wherein the non-peptidyl polymer reacts with the physiologically active polypeptide in step (1), and the complex of physiologically active polypeptide-non-peptidyl polymer of step (1) reacts with the immunoglobulin constant region in step (2).

12. The method according to claim 11, wherein the physiologically active polypeptide and the non-peptidyl polymer react with each other at a molar ratio of 1:1 to 1:20 in step (1), and the product of step (1) and the immunoglobulin constant region react with each other at a molar ratio of 1:0.5 to 1:10 in step (2).

13. The method according to claim 12, wherein step (2) is carried out in the presence of sodium chloride added at a final concentration of 0.5 to 2.5 M, sodium acetate added at a final concentration of 0.3 to 2.0 M, sodium sulfate added at a final concentration of 0.4 to 0.6 M, sodium phosphate added at a final concentration of 0.4 to 0.6 M, or potassium chloride added at a final concentration of 0.5 to 1.0 M.

14. The method according to claim 1, wherein the non-peptidyl polymer is polyethylene glycol.

15. The method according to claim 1, wherein the non-peptidyl polymer has a molecular weight ranging from 1 to 100 kDa.

16. The method according to claim 1, wherein the immunoglobulin constant region is aglycosylated.

17. The method according to claim 1, wherein the immunoglobulin constant region consists of one to four domains selected from the group consisting of CH1, CH2, CH3 and CH4 domains.

18. The method according to claim 1, wherein the immunoglobulin constant region further comprises a hinge region.

19. The method according to claim 1, wherein the immunoglobulin constant region is selected from the group consisting of constant regions from IgG, IgA, IgD, IgE, IgM, a combination thereof, and a hybrid thereof.

20. The method according to claim 1, wherein the immunoglobulin constant region is selected from the group consisting of constant regions of IgG1, IgG2, IgG3, IgG4, a combination thereof, and a hybrid thereof.

21. The method according to claim 20, wherein the immunoglobulin constant region is an IgG4 Fc region.

22. The method according to claim 21, wherein the immunoglobulin constant region is an aglycosylated human IgG4 Fc region.

23. The method according to claim 1, wherein the physiologically active polypeptide is selected from the group consisting of a human growth hormone, a growth hormone releasing hormone, a growth hormone releasing peptide, an interferon, an interferon receptor, a colony-stimulating factor, a glucagon-like peptide (GLP-1), oxyntomodulin, a G protein-coupled receptor, an interleukin, an interleukin receptor, an enzyme, an interleukin-binding protein, a cytokine-binding protein, a macrophage activating factor, a macrophage peptide, a B-cell factor, a T-cell factor, Protein A, a cell necrosis glycoprotein, an immunotoxin, a lymphotoxin, tumor necrosis factor, a tumor suppressor, transforming growth factor, alpha-1 anti-trypsin, albumin, α-lactalbumin, apolipoprotein-E, erythropoietin, glycosylated erythropoietin, an angiopoeitin, hemoglobin, thrombin, a thrombin receptor activating peptide, thrombomodulin, blood factor VII, VIIa, VIII, IX and XIII, a plasminogen activator, a fibrin-binding peptide, urokinase, streptokinase, hirudin, Protein C, C-reactive protein, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, follicle stimulating hormone, luteinizing hormone, luteinizing hormone releasing hormone, a nerve growth factor, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, and myostatin.

24. The method according to claim 23, wherein the physiologically active polypeptide is insulin.

25. The method according to claim 1, wherein in step (1), the physiologically active polypeptide and the non-peptidyl polymer react with each other at a molar ratio of 1:1 to 1:20 under the pH condition of 5.0 to 6.5, and in step (2), the reaction mixture of step (1) and the immunoglobulin constant region react with each other at a molar ratio of 1:0.5 to 1:10 in the presence of the salt; wherein the salt is sodium chloride, which is added at a final concentration of 0.5 to 2.5 M; sodium acetate which is added at a final concentration of 0.3 to 2.0 M; sodium sulfate which is added at a final concentration of 0.4 to 0.6 M; sodium phosphate which is added at a final concentration of 0.4 to 0.6 M; or potassium chloride which is added at a final concentration of 0.5 to 1.0 M.

26. The method according to claim 1, wherein the non-peptidyl polymer of the complex has an aldehyde functional group at its end, which is to be linked to an amine group which is present at an N-terminus or on a side chain of Lys residue of the physiologically active polypeptide or the immunoglobulin constant region to form the conjugate.

27. The method according to claim 1, wherein the physiologically active polypeptide is insulin, and the non-peptidyl polymer is polyethylene glycol.

28. The method according to claim 1, wherein
the chloride salt is sodium chloride, potassium chloride, magnesium chloride, ammonium chloride, or calcium chloride;
the acetate salt is sodium acetate, potassium acetate, magnesium acetate, ammonium acetate, or calcium acetate;
the sulfate salt is sodium sulfate, potassium sulfate, magnesium sulfate, ammonium sulfate, or calcium sulfate; and
the phosphate salt is sodium phosphate, potassium phosphate, magnesium phosphate, ammonium phosphate, or calcium phosphate.

* * * * *

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```